United States Patent [19]

Transue

[11] 4,450,839

[45] May 29, 1984

[54] SURGICAL CLIP APPLIER WITH SERPENTINE SPRING CLIP FEEDER

[75] Inventor: James A. Transue, Union, N.J.

[73] Assignee: Ethicon, Inc., Somerville, N.J.

[21] Appl. No.: 352,833

[22] Filed: Feb. 26, 1982

[51] Int. Cl.³ .............................................. A61B 17/12
[52] U.S. Cl. ................................ 128/325; 227/DIG. 1
[58] Field of Search .................... 128/325, 326, 334 R, 128/335, 335.5, 346; 227/DIG. 1, 19, DIG. 1 A, DIG. 1 B, DIG. 1 C, 117, 125; 29/243.56; 72/410

[56] References Cited

U.S. PATENT DOCUMENTS

| | | | |
|---|---|---|---|
| 2,733,441 | 2/1956 | White | 227/DIG. 1 B |
| 3,006,344 | 10/1961 | Vogelfanger | 128/346 |
| 3,082,426 | 3/1963 | Miles | 72/410 X |
| 3,780,416 | 12/1973 | Rider | 128/334 R X |
| 4,166,466 | 9/1979 | Jarvik | 227/19 X |
| 4,201,314 | 5/1980 | Samuels et al. | 227/DIG. 1 X |
| 4,226,242 | 10/1980 | Jarvik | 128/325 |
| 4,316,468 | 2/1982 | Klieman et al. | 128/335 X |
| 4,325,376 | 3/1982 | Klieman et al. | 128/335 X |
| 4,372,316 | 2/1983 | Blake et al. | 128/325 |
| 4,380,238 | 3/1983 | Colucci et al. | 128/325 X |

Primary Examiner—C. Fred Rosenbaum
Assistant Examiner—Michelle N. Lester
Attorney, Agent, or Firm—Robert L. Minier

[57] ABSTRACT

An instrument is provided for applying ligating clips seriatim and includes first and second handles mounted together for pivotal movement. Each handle extends beyond the pivot axis to form a clip closing jaw. The first handle includes a guideway for receiving a plurality of open clips. A pushing mechanism motivated by a serpentine spring is provided within the first handle to feed the clips to the jaw region. One of the jaws includes a lip for preventing discharge of the open front clip from the instrument. A mechanism is provided for at least temporarily maintaining the spring in a compressed position to permit loading of the instrument with clips and to permit transport and storage of the instrument without the feeding force acting on the clips.

11 Claims, 8 Drawing Figures

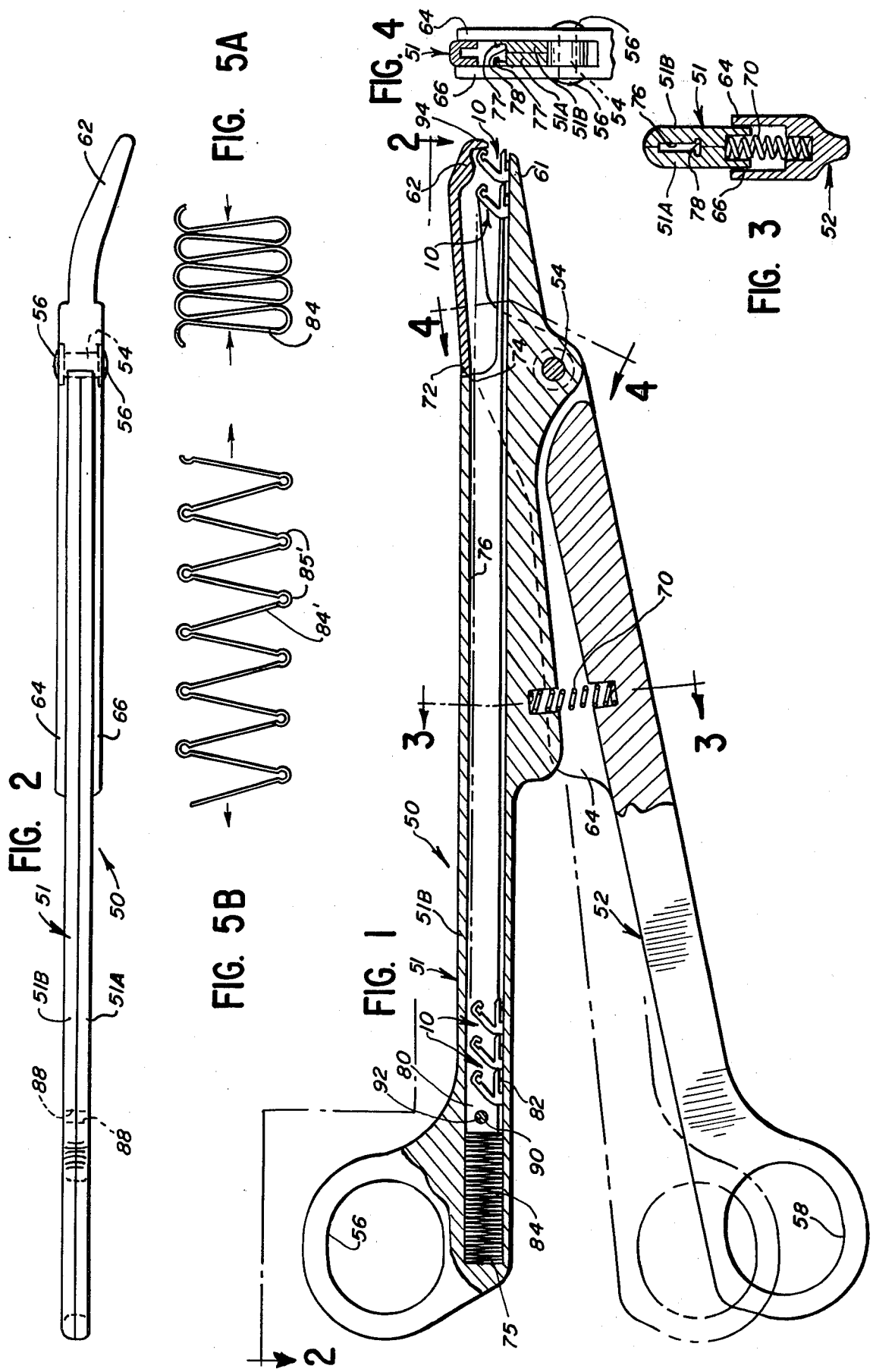

SURGICAL CLIP APPLIER WITH SERPENTINE SPRING CLIP FEEDER

TECHNICAL FIELD

This invention relates to a surgical instrument for repeatedly applying surgical clamps or clips to tissue, blood vessels, and the like.

BACKGROUND OF THE INVENTION

Clips have been devised for clamping or strangulating various organs, vessels, and other tissue. Clips have been developed for use specifically in strangulating blood vessels in the human body. Such clips are known as hemostatic or ligating clips. The clips may be fabricated from absorbable or nonabsorbable polymeric materials as well as from metal.

A ligating clip is typically C-shaped, U-shaped, or V-shaped with two spaced-apart or diverging legs connected together at one end in a manner that permits the clip to be squeezed together so that the legs of the clip may be clamped around the tissue or blood vessel so as to tightly constrict the tissue or blood vessel. This prevents a substantial amount of fluid from passing through the tissue or blood vessel from one side of the closed clip to the other side of the closed clip.

Typically, the clip is made of a material and/or has a configuration that enables the clip, once it has been forced closed, to remain set or latched closed and maintain the closed orientation without outside intervention. For example, if the clip is made from a metal material, the clip can be deformed to the closed position. If the clip is made from a thermoplastic material, the legs may be connected by a resilient hinge portion and the distal ends of the legs may be provided with latch means for holding the legs together in a closed position when the legs of the clip are squeezed together around the tissue or blood vessel.

A variety of instruments for applying such surgical clips have been developed or proposed in the past. A number of such instruments are discussed and disclosed in the copending patent application Ser. No. 208,368 filed on Nov. 19, 1980. Such instruments typically include a magazine or cartridge which may or may not be disposable and which holds a plurality of clips. The clips are supplied from the cartridge to jaws of the instrument one at a time for application to the tissue or blood vessel.

U.S. Pat. No. 3,006,344 discloses an instrument for applying a ligating clip to a blood vessel. The clip is formed of flat metal or like stock and has a pair of legs extending outwardly in a generally V-shape. The clips are arranged in two parallel grooves in a magazine. A slide is positioned in each groove and is urged by a suitable conventional spring to advance the clips along the magazine toward the jaws. The clips are arranged in each row with one end of one clip abutting the connecting rear portion of the next adjacent front clip. The clips are not nestably arranged with the connecting portion of each clip received between the open legs of the next adjacent clip. Rather, the distal end of one of the legs of one clip abuts the rear connecting portion of the next adjacent clip.

U.S. Pat. No. 3,753,438 discloses an applicator for applying clips to suturing thread during the suturing of skin wounds. The clips are carried in a cartridge in the instrument. A clip is forced forwardly from the cartridge to a position between the instrument jaws by a slide which is operated by a handle. After the clip is positioned within the jaws, the handles of the instrument are squeezed together to squeeze the clip legs together.

U.S. Pat. No. 2,968,041 discloses a trigger actuated "gun" type of clip applicator wherein a flat, sinuous, stainless steel spring is provided to close the jaws when the trigger is pulled. However, the clips are merely loosely contained in a magazine and slide forward in the applicator under the influence of gravity when the applicator is tilted.

It would be desirable to provide an improved instrument for accommodating a plurality of clips and for automatically feeding the clips seriatim into jaws where the clips may be compressed about tissue, such as blood vessels and the like.

It would also be desirable to provide an instrument for applying clips wherein the clips could be arranged in a relatively compact orientation in order to provide an efficient and economical structure.

It would be beneficial if the instrument could be provided with means for biasing the clips forwardly to the jaws but in a manner that would prevent the front clip from being urged or biased against the tissue. This would avoid imposition of an undesired force on the tissue during application of the clip.

It would be advantageous to provide such an instrument with means for releasing the forward biasing force at least temporarily to permit reloading of the instrument with new clips.

It would also be desirable to provide an instrument for applying ligating clips in which the instrument could be actuated by means of scissors-type handles in the same manner as a number of other widely used surgical instruments and in the manner to which surgeons have become accustomed over the years.

SUMMARY OF THE INVENTION

A preferred embodiment of the present invention is incorporated in a medical instrument for applying clips, including ligating clips made from a thermoplastic material. The clips each typically have two legs connected together at one end of the clip and are adapted to assume an initial open or spread-apart configuration at the other end.

In the preferred embodiment, the ligating clips are made from a thermoplastic material and that have first and second legs joined at their proximal ends by a resilient hinge. The clip legs are spaced apart at their distal ends and each leg has a latch means at its distal end to engage the other leg of the clip for holding the clip closed in clamping engagement about tissue, such as a blood vessel, when the legs are squeezed together.

Each clip includes a base extending along at least a portion of the first leg and includes means for being guided, by for being retained by, and for supporting the clip in, the instrument.

The instrument includes first and second handles mounted together for pivotal movement about a pivot axis. Each handle extends forwardly beyond the pivot axis to form a clip closing jaw. The jaws have opposing clip engaging faces.

Means associated with the first and second handles is provided for limiting the pivoting movement of the handles to a maximum opening of the jaws.

The first handle includes a guideway for receiving a plurality of open clips in a single row with the clips arranged in end-to-end relationship with the distal end of the first end of one clip abutting the hinge of the next forwardly adjacent clip. The first handle includes a clip retaining means along the guideway for engaging the clip base to retain the clip in sliding engagement with the first handle in the guideway.

Means is provided on the second handle jaw for engaging the second leg of the front clip in the row of clips when the jaws are at the maximum opening and when the open front clip is positioned between the open jaws whereby discharge of the front clip from the open jaws is prevented.

A last clip engaging member is disposed within the guideway and is adapted to bear against the last clip in the row of clips.

A serpentine spring is disposed within the guideway and is adapted to be compressed behind the last clip engaging member for moving the row of clips forwardly along the guideway to the jaws.

The invention of the apparatus herein described resides in the novel combination, construction, arrangement, and disposition of various component parts and elements incorporated in the apparatus in accordance with the principles of the invention.

The present invention will be better understood and important features other than those specifically enumerated above will become apparent when consideration is given to the following details and description which, when taken in conjunction with the drawings, describes, discloses, illustrates, and shows a preferred embodiment of the present invention and what is presently believed to be the best mode of practicing the principles of the invention. Other embodiments and modifications may be suggested to those having the benefit of the teachings herein, especially as they fall within the scope and spirit of the sub-joined claims.

BRIEF DESCRIPTION OF THE DRAWINGS

In the accompanying drawings forming part of the specification and in which like numerals are employed to designate like parts throughout the same, FIG. 1 is a top plan view of the instrument of the present invention with portions of the structure broken away to permit illustration of interior details and showing the instrument fully open in solid lines and showing the closed position of the instrument handles in dashed lines;

FIG. 2 is a side view of the instrument of the present invention as viewed along the planes 2—2 in FIG. 1;

FIG. 3 is a cross-sectional view taken generally along the plane 3—3 in FIG. 1;

FIG. 4 is an enlarged, fragmentary, cross-sectional view taken generally along the plane 4—4 in FIG. 1;

FIG. 5A is a greatly enlarged, fragmentary, side view of one form of a spring for the instrument;

FIG. 5B is a greatly enlarged, fragmentary, side view of another form of a spring for the instrument;

DESCRIPTION OF THE PREFERRED EMBODIMENT

This invention may be used in many different forms. The specification and the accompanying drawings discloses a specific embodiment as an example of the use of the invention. The invention is not intended to be limited to the embodiment illustrated, and the scope of the invention will be pointed out in the appended claims.

The precise shapes and sizes of the components herein described are not essential to the invention unless otherwise indicated. The particular shapes and sizes are shown to best illustrate the principles of the invention.

A variety of materials may be used for constructing the illustrated instrument as those skilled in the art will appreciate.

Figure 6:
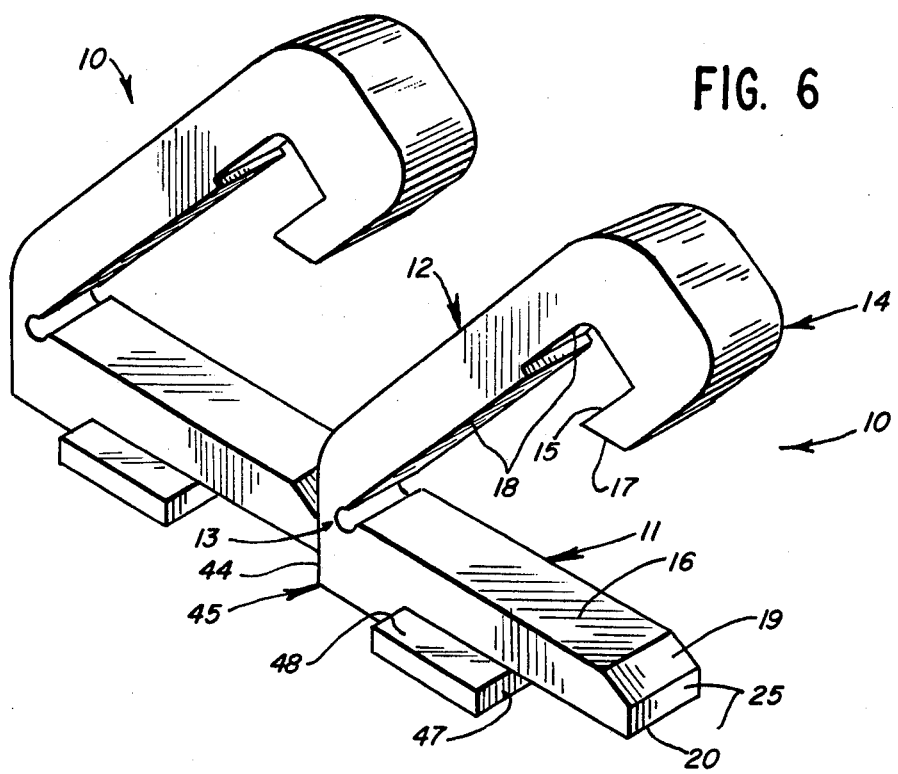
FIG. 6 is a perspective view of a first embodiment of a surgical clip which may be applied to tissue with the instrument of the present invention.

One type of clip or clamp that may be applied with the instrument of the present invention is shown in FIG. 6 and is designated therein generally by the reference numeral 10. Two clips 10 are illustrated as being open and aligned end-to-end in a row as they would be positioned in the instrument of the present invention that is described in detail hereinafter.

The clip 10 is seen to be formed with two legs or leg segments 11 and 12 connected at the proximal ends thereof by a hinge, a hinge portion, or a hinge section 13. The leg segment 12 terminates at the distal end 13 thereof in a hook member 14 having an inner face 15 substantially parallel to an inner face 18 of the leg segment 12 and forming an acute angle with an end face 17.

The leg segment 11 terminates at the distal end in an end face 19 which forms an obtuse angle with an inner face 16 of the leg segment 11. Additionally, the leg segment 11 is squared off at a face 25 to form a substantially right angle with a bottom face 20.

The length and width of the inner faces 16 and 18 are substantially equal and the face 15 of the hook member 14 is spaced from the inner face 18 of the leg segment 12 by a distance corresponding to the thickness of the leg segment 11 between the planes of the inner face 16 and the bottom face 20.

When the leg segments 11 and 12 are pivoted about the hinge section 13 to bring the inner faces 18 and 16 into opposition, the hook member 14 is deflected by the end face 19 of the leg segment 11 until the distal end of the leg segment 11 snaps under the hook member 14 and is thereby locked in place. The end face 17 of the hook member 14 and the end face 19 of the leg segment 11 are angled as illustrated in FIG. 6 to facilitate the passage of the hook member 14 past the leg segment 11 during clip closure.

The surfaces of the inner faces 16 and 18 may be smooth as illustrated in FIG. 6, or may be provided with ridges or grooves to increase vessel holding power. The leg segment 12 may also be undercut at the juncture of the hook member 14 and the inner face 18 as illustrated in FIG. 6 to increase the deflectability of the hook member 14 and increase the space between the hook member 14 and the leg segment 12. This compensates for any inward deflection of the hooked member 14 during closure which might reduce the clearance between the surfaces 15 and 18 and otherwise interfere with the latching of the clip.

The clip 10 also has a novel base 45 extending along a portion of either one of the two legs, such as the first leg 11 as illustrated. The base 45 terminates in a front face 47 short of the distal end of the first leg 11 whereby an open recess is defined adjacent the front face 47 and below the first leg 11. The recess provides clearance for latching the hook member 14.

Flanges 48 are provided on a portion of the base 45. The flanges 48 extend rearwardly from a front face 47 and terminate short of the first leg proximal end. The flanges 48 extend laterally outwardly beyond both sides of the first leg 11 to function as guide means for engaging portions of the instrument as will be explained in detail hereinafter. The portion of the base that extends rearwardly from the flanges 48 to the proximal end of the clip first leg 11 has a width not greater than the width of the first leg 11.

The rear end of clip 10, including the hinge section 13 and the back of the base 45, defines a flat surface 44. Thus, the first leg front face 25 of one clip can abut the rear surface 44 of the next forwardly adjacent clip when the clips are open and arranged end-to-end in a row.

Figure 7:
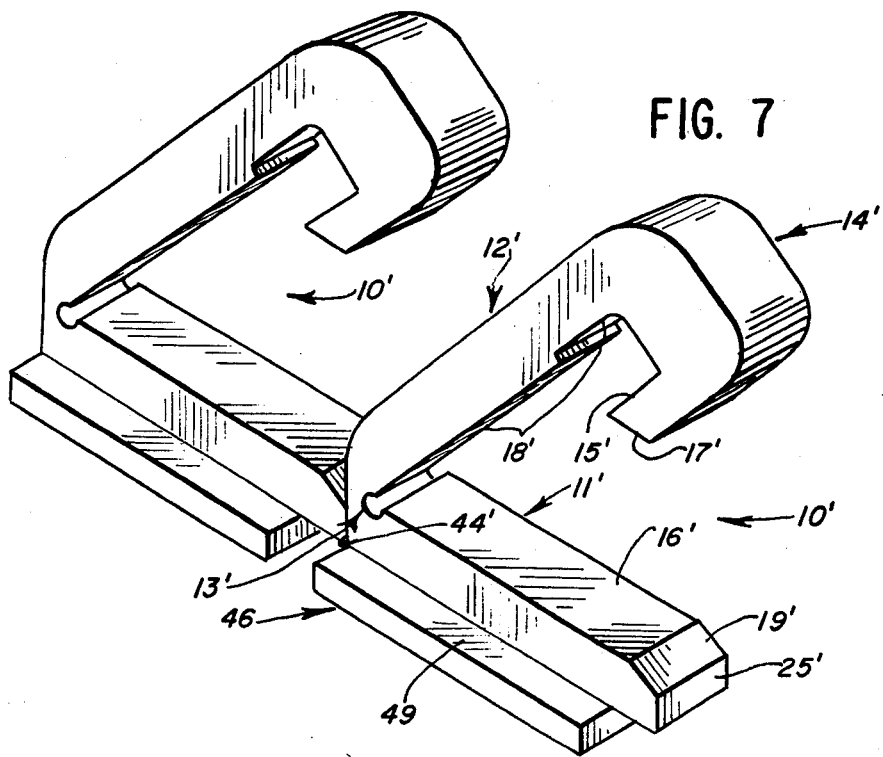
FIG. 7 is a perspective view of another embodiment of a surgical clip which may be applied with instrument of the present invention.

A second form of a ligating clip that may be used with the instrument of the present invention is illustrated in FIG. 7 and is designated generally therein by reference numeral 10'. Two clips 10' are illustrated as being opened and aligned end-to-end in a row as they would be positioned in the instrument of the present invention that is described in detail hereinafter.

Each clip 10' has a basic structure substantially similar to that of the clip 10 described above with reference to FIG. 6, except for the base portion 46 of clip 10' which is different than the base 45 of the clip 10. The features of clip 10', other than the base 46, are substantially identical in configuration and function to the features of clip 10 illustrated in FIG. 6. Accordingly, the structural features of clip 10' of FIG. 7 that are identical to structural features of clip 10 of FIG. 6 are designated by the same reference numerals used in FIG. 6 for clip 10, but with the addition of a prime mark following each such reference numeral.

The base 46 of clip 10' extends rearwardly along the length of the first leg 11' to the end of the first leg 11'. The base 46 serves to support the clip in the instrument of the present invention that may be used to apply the clip 10' and which is described in detail hereinafter. The base 46 also serves for being engaged by and for being guided by the instrument. The base 46 terminates short of the distal end of the first leg 11' to define a recess for accommodating the latching of the hook member 14' of the second leg 12'.

The base 46 has a generally right rectangular parallelpiped or prism configuration with portions 49 extending laterally outwardly from the first leg 11' on each side of the first leg. The portions 49 of the base 46 extending laterally outwardly function as a guide means for engaging portions of the clip applier instrument.

Each of the above-described two novel clip structures, when fabricated from a suitable thermoplastic material, is biased to the open position by the resilient hinge portion. Thus, if force is applied to the distal ends of the legs of the open clip so as to move the legs toward one another (but not far enough to latch the clip), then upon removal of the force from the clip legs, the clip legs will return to the substantially fully open orientation.

It is believed that this phenomenon can be used to advantage in certain types of clip applier instruments for guiding and holding the clip in the instrument. Specifically, the legs of the clip may be deflected inwardly toward one another a small amount in a magazine, guide channel, or jaw structure of a clip applier instrument. Owing to the resilience of the hinge joining the two legs, the two legs will exert a force outwardly against the magazine, channel, or jaw structure to thereby provide a small friction holding force which may serve to help maintain the clip in the proper orientation or position within the instrument.

The above-described action of the resilient hinge plastic clip is in contrast with conventional ligating clips fabricated from relatively small diameter wire-like stock. Such metal clips can tolerate substantially no inward deflection of the legs without undergoing permanent deformation. Consequently, such metal clips exhibit no useful degree of resiliency and thus do not have the same inherent capability for providing the frictional holding force that is found in the above-described type of plastic clip.

FIG. 1 illustrates one form of an instrument 50 of the present invention for applying clips, such as the ligating clips 10 and 10' described above with reference to FIGS. 6 and 7. The instrument 50 includes a first scissors-type handle 51 and a second scissors-type handle 52 that are mounted together for pivotal movement, about a pivot axis defined by a pin or a shaft 54, between an open position and a closed position. The shaft 54 has a head 56 on either side of the second handle 52 as best illustrated in FIGS. 2 and 4.

The first handle 51 extends rearwardly of the pivot shaft 54 and includes a finger or thumb ring 56. Similarly, the second handle 52 extends rearwardly of the pivot shaft 54 and includes a finger or thumb ring 58.

The first handle 51 extends forwardly of the pivot shaft 54 and defines a lower jaw 61. Similarly, the second handle 52 extends forwardly of the pivot shaft 54 and defines an upper jaw 62.

As best illustrated in FIGS. 1, 2, and 3, the second handle 52 includes a pair of spaced-apart sidewalls 64 and 66 which extend for a portion of the length of the second handle 52 and which merge above the pivot shaft 54 to form the upper jaw 62. Preferably, as best illustrated in FIG. 2, a substantial portion of the length of each of the handles 51 and 52 lies in a common plane. However, the jaws 61 and 62 curve laterally outwardly.

Preferably, means is provided for biasing the first and second handles 51 and 52, respectively, to a fully open position as illustrated in solid line in FIG. 1. Specifically, the biasing means is designated generally by reference numeral 70 in FIGS. 1 and 3 and is preferably a helical compression spring disposed between the first and second handles 51 and 52, respectively, rearwardly of the pivot shaft 54.

The spring 70 biases the handles 51 and 52 apart, and hence the jaws 61 and 62, to a maximum opening as determined by a means associated with the first and second handles for limiting the pivoting movement. Specifically, with reference to FIG. 4, the means associated with the first and second handles for limiting the pivoting movement of the handles includes an abutment surface 72 on the first handle 51 and an engaging surface 74 on the second handle 52. The second handle engaging surface 74 is oriented at an angle relative to the first handle abutment surface 72 when the handles 51 and 52 are closed. However, when the handles are opened to the maximum opening of the jaws illustrated in FIG. 1, the surface 74 is oriented substantially parallel with, and is in contact with, the first handle abutment surface 72.

As best illustrated in FIGS. 2 and 3, the first handle 51 includes two mating pieces or halves 51A and 51B which are secured together by a suitable conventional means, such as by screws or snap-fit connections (not illustrated).

The first handle halves 51A and 51B define a chamber, channel, or guideway 76 as best illustrated in FIGS. 1 and 3. The upper portion of the guideway 76 has a generally rectangular cross section that communicates along its bottom with a lower channel 78 that is wider than the upper part of the guideway 76. The guideway 76 receives a plurality of the open clips (e.g., clip 10 of FIG. 6) in end-to-end relationship with the distal end of the first leg of one clip abutting the leg connection end or hinge of the next forwardly adjacent clip. The clips 10 are moved forwardly along the guideway 76 by means described hereinafter in detail.

As best illustrated in FIGS. 3 and 4, the lower or bottom channel 78 receives the clip base 45 and base flanges 48 of each clip 10. The interior portions of the handle 51 that define the upper part of the guideway 76 above the lower channel 78 project inwardly over the lower channel 78 and function as a clip retaining means along the guideway for engaging the clip flanges 48 to retain the clips in sliding engagement with the first handle 51 in the guideway 76.

As best illustrated in FIG. 1, the guideway 76 is defined at the rear end of the handle 51 by a rear wall 75. The upper sides of the first handle 51 that define the guideway 76 do not extend forwardly beyond the handle pivot shaft 54. In the region of the jaw 61, the opening into the channel 78 is defined by inwardly projecting flanges 77 on either side as best illustrated in FIG. 4. These flanges 77 thus continue to retain the clips within the channel 78 forward of the pivot shaft 54.

The clips 10 are moved forwardly along the guideway 76 to the region of the jaws 61 and 62 by a novel pusher mechanism. Specifically, a last clip engaging member 80 is disposed within the guideway 76 and is adapted to bear against the last clip in the row of clips. Preferably, the last clip engaging member 80 defines a bearing surface 82 conforming to the exterior, rearwardly facing surfaces of at least a portion of the second leg and hinge of the last clip when the last clip is in the open position as illustrated in FIG. 1. With reference to FIG. 6, the rear surface 44 of the clip 10, as well as the exterior surface of the leg 12 of the clip 10, would be engaged by the member 80.

A flat, serpentine spring 84 is disposed within the guideway 76, against rear wall 75, and is adapted to be compressed behind the last clip engaging member 80 for moving the row of clips forwardly along the guideway 76 to the jaws 61 and 62. Preferably, the flat, serpentine spring 84 has a relatively high compression ratio and one end may be secured to, or at least bear against, the last clip engaging member 80.

The serpentine spring 84, generally occupying a volume in the shape of a right rectangular prism, is conveniently received and captured in the clip guideway 76, thus eliminating the necessity for providing suitable guiding structures that might be required if another type of spring were used.

The serpentine spring 84 is shown in a compressed state in FIG. 1. FIG. 5A is an enlarged view of the serpentine spring 84 also in the compressed state. In a specific embodiment of the instrument 50, such as illustrated in FIG. 1, the spring 84 may be made from a suitable flat spring stock (e.g., ASTM A228-47) having a thickness of about 0.003 inch. Such a spring 84 preferably has a closed pitch of 0.036 inch and an open pitch of 0.385 inch. When the spring 84 is in the open, uncompressed state, the height of the spring is 0.187 inch, the radius at each bend is about 0.015 inch, and the angle between the two diverging legs at each bend is about 90 degrees.

FIG. 5B illustrates an alternate embodiment of a spring 84', shown in an open (uncompressed) state, which functions in a manner similar to the spring 84 illustrated in FIG. 5A. Each pair of diverging legs in the spring 84' is joined by a circular arc bend 85'. When the spring 84' is in the open, uncompressed state as illustrated, the bend defines an arc 85' greater than 180 degrees but the legs diverge from the arc at an included angle of less than 90°.

Other suitable serpentine spring designs may be used instead of the designs illustrated in FIGS. 5A and 5B.

As best illustrated in FIGS. 1 and 2, the first handle half 51A and the first handle half 51B each define a bore 88. The bores 88 of the first handle halves 51A and 51B are aligned on a common longitudinal axis and each bore 88 extends through the handle half from the exterior of the handle to the guideway 76.

The last clip engaging member 80 defines a transverse bore 90 (FIG. 1) that can be aligned with the first handle bores 88 by locating the last clip engaging member 80 in the guideway 76 as illustrated in FIG. 1 wherein the spring 84 is substantially compressed. With the member 80 at this position, a pin 92 can be at least temporarily disposed through the first handle bores 88 and through the last clip engaging member bore 90 so as to lock the last clip engaging member 80 at that position. This permits the portion of the guideway 76 that is forward of the last clip engaging member 80 to be loaded with a plurality of the open clips 10.

The clips 10 may be loaded into the instrument 50 by pushing the clips 10 rearwardly through the open jaws. The second leg of each open clip will be temporarily deflected toward the first leg as the clip is forced past the jaws. Alternatively, the clips may be loaded into the instrument during the initial fabrication of the instrument before the two first handle halves 51A and 51B are secured together. Also, the instrument can be designed for easy disassembly (by removing the pivot shaft 54, removing the first handle 51 from the second handle 52, and by then separating the first handle halves 51A and 51B). This would permit loading of the clips into the disassembled instrument.

In addition to facilitating the loading of the instrument with open clips, the above-described temporary locking mechanism permits the fully loaded instrument to be stored and/or transported without the spring load being imposed upon the clips 10. When the instrument is to be used, the pin 92 is removed to permit the spring to establish the forward biasing force on the row of clips in the instrument.

The second handle upper jaw 62 includes means for engaging the second leg of the front clip in the row of clips when the jaws 61 and 62 are at the maximum opening (FIG. 1) and when the front clip is open and positioned between the open jaws. This prevents discharge of the open front clip from the open jaws. Specifically, the engaging means on the second handle upper jaw 62 includes a downwardly projecting lip 94 as best illustrated in FIG. 1. The lip 94 extends forwardly beyond the distal end of the first handle lower jaw 61 and would overlap the lower jaw 61 if the jaws were closed without a clip between the jaws.

When the instrument is opened so that the jaws 61 and 62 are at the maximum opening as illustrated in FIG. 1, the lip 94 prevents the front clip from being discharged from the instrument until the front clip is latched closed. When the front clip is latched closed, the height of the closed clip is less than the maximum opening of the jaws 61 and 62 so that the closed clip can be discharged from the instrument when the jaws are subsequently opened to release the closed clip.

In normal operation, the instrument 50 is actuated by closing the handles 51 and 52 to latch closed the front clip about a blood vessel or other tissue. Subsequent opening of the handles, and withdrawal of the instrument 50 rearwardly, effects a complete discharge of the latched closed clip from the jaws and permits the next rearwardly adjacent clip to be fed forwardly, along with the entire row of clips. With the next clip in position at the jaws and retained by the second jaw lip 94, the instrument 50 is again ready for applying the next clip.

After all of the clips 10 have been applied, the last clip engaging member 80 advances into the region between the jaws 61 and 62. Preferably, the last clip engaging member 80 is fabricated from a substantially rigid material and resists any attempt to further close the jaws. This signals the surgeon that all of the clips have been used.

Although the instrument 50 has been described above as being adapted to apply clips having the configuration of clips 10 and 10' illustrated in FIGS. 6 and 7, it is to be realized that clips having other suitable configurations may be applied with the instrument. For example, metal hemostatic clips with appropriate base structures may be utilized. Such clips, while not having resilient hinges, may be formed of tantalum or stainless steel. These clips could be deformed into the closed position and would possess sufficient strength to retain the deformation when clamped about a duct, such as a blood vessel.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A scissors-type medical instrument for repeatedly applying a plurality of ligating clips seriatim about tissue wherein each said clip is initially provided in an open state and wherein each said clip comprises first and second legs joined at their proximal ends by a resilient hinge and spaced apart at their distal ends with said legs having latch means at said distal ends for holding said clip closed in clamping engagement about said tissue when said legs are squeezed together; each said clip including a base extending along at least a portion of said first leg and including means for being guided and retained by, and for supporting said clip in, said instrument; said instrument comprising:

first and second handles mounted together for pivotal movement about a pivot axis, each said handle extending forwardly beyond the pivot axis to form a clip closing jaw, said jaws having opposing clip engaging faces;

means associated with said first and second handles for limiting the pivoting movement of said handles to a maximum opening of said jaws;

said first handle including a guideway for receiving a plurality of said open clips in a single row with the clips arranged in end-to-end relationship with the distal end of said first leg of one clip abutting the hinge of the next forwardly adjacent clip, said first handle including clip retaining means along said guideway for engaging said clip base to retain said clip in sliding engagement within said first handle in said guideway;

means on said second handle jaw for engaging said second leg of the front clip in said row of clips when said jaws are at said maximum opening and when the front clip is open and positioned between the open jaws whereby discharge of the open front clip from the open jaws is prevented;

a last clip engaging member disposed within said guideway and adapted to bear against the last clip in said row of clips; and a serpentine spring disposed within said guideway and adapted to be compressed behind said last clip engaging member for moving said row of clips forwardly along said guideway to said jaws.

2. The instrument in accordance with claim 1 in which said last clip engaging member is engaged by the forward end of said spring and in which a forward end of said last clip engaging member defines a bearing surface conforming to the exterior, rearwardly facing surfaces of at least a portion of said second leg and hinge of one of said clips when said one clip is open.

3. The instrument in accordance with claim 1 in which said first handle defines at least one transverse hole through the first handle from the exterior of the first handle to said guideway and in which said last clip engaging member defines a transverse hole that can be aligned with said first handle transverse hole by locating said last clip engaging member at a predetermined position in said guideway wherein (1) said spring is substantially compressed and (2) a pin can be disposed through said first handle transverse hole and through said last clip engaging member transverse hole for at least temporarily locking said last clip engaging member at said predetermined position to permit the portion of the guideway forward of said last clip engaging member to be loaded with a plurality of open clips.

4. The instrument in accordance with claim 1 further including means for biasing said first and second handles apart a distance sufficient to open said jaws to said maximum opening.

5. The instrument in accordance with claim 4 in which said handle biasing means includes a helical compression spring disposed between said first and second handles rearwardly of said pivot axis.

6. The instrument in accordance with claim 1 in which said instrument is adapted to apply clips in which at least a portion of the base of each said clip extends laterally outwardly from said first leg and in which said instrument clip guideway includes a lower channel defined by inwardly projecting portions of said first handle that extend over said laterally extending portions of the clip bases to aid in retaining the clips in the instrument.

7. The instrument in accordance with claim 1 in which each of said first and second handles includes a substantial portion lying substantially in a common plane and in which said jaws curve laterally out of said common plane.

8. The instrument in accordance with claim 1 in which said means on said second handle jaw for engaging said clip second leg includes a downwardly projecting lip that extends forwardly beyond the distal end of said first handle jaw.

9. The instrument in accordance with claim 1 in which said last clip engaging member is fabricated from a substantially rigid material and is adapted to enter into the region between said jaws after all of the clips have been discharged from said instrument whereby subsequent closure of said jaws is prevented.

10. The instrument in accordance with claim 1 in which said means associated with said first and second handles for limiting the pivoting movement of said handles includes an abutment surface on said first handle and an engaging surface on said second handle, said second handle engaging surface being oriented at an angle relative to said first handle abutment surface when said handles are closed and being substantially parallel with said first handle abutment surface when said handles are opened to said maximum opening of said jaws.

11. A scissors-type medical instrument for repeatedly applying a plurality of ligating clips seriatim about tissue wherein each said clip is initially provided in an open state and wherein each said clip comprises first and second legs which are joined at a leg connection end of the clip and which are spaced apart at their distal ends; each said clip including a base extending along at least a portion of said first leg and including means for being guided and retained by, and for supporting said clip in, said instrument; said instrument comprising:

first and second handles mounted together for pivotal movement about a pivot axis, each said handle extending forwardly beyond the pivot axis to form a clip closing jaw, said jaws having opposing clip engaging faces;

means associated with said first and second handles for limiting the pivoting movement of said handles to a maximum opening of said jaws;

said first handle including a guideway for receiving a plurality of said open clips in a single row with the clips arranged in end-to-end relationship with the distal end of said first leg of one clip abutting the leg connection end of the next forwardly adjacent clip, said first handle including clip retaining means along said guideway for engaging said clip base to retain said clip in sliding engagement within said first handle in said guideway;

means on said second handle jaw for engaging said second leg of the front clip in said row of clips when said jaws are at said maximum opening and when the front clip is open and positioned between the open jaws whereby discharge of the open front clip from the open jaws is prevented;

a last clip engaging member disposed within said guideway and adapted to bear against the last clip in said row of clips; and a serpentine spring disposed within said guideway and adapted to be compressed behind said last clip engaging member for moving said row of clips forwardly along said guideway to said jaws.

* * * * *